(12) United States Patent
Ferrero et al.

(10) Patent No.: US 9,309,621 B2
(45) Date of Patent: Apr. 12, 2016

(54) PROCESS FOR ACETIC ACID REMOVAL FROM PRETREATED BIOMASS

(75) Inventors: Simone Ferrero, Tortona (IT); Paolo Corbellani, Tortona (IT)

(73) Assignee: Beta Renewables, S.p.A., Tortona (AL) (IT)

( * ) Notice: Subject to any disclaimer, the term of this patent is extended or adjusted under 35 U.S.C. 154(b) by 0 days.

(21) Appl. No.: 14/111,905

(22) PCT Filed: May 17, 2012

(86) PCT No.: PCT/IB2012/052490
§ 371 (c)(1),
(2), (4) Date: Oct. 15, 2013

(87) PCT Pub. No.: WO2012/156941
PCT Pub. Date: Nov. 22, 2012

(65) Prior Publication Data
US 2014/0034253 A1    Feb. 6, 2014

(30) Foreign Application Priority Data
May 18, 2011  (IT) .............................. TO2011A0441

(51) Int. Cl.
| | | |
|---|---|---|
| *D21C 1/02* | (2006.01) | |
| *D21C 1/04* | (2006.01) | |
| *D21B 1/02* | (2006.01) | |
| *D21C 11/00* | (2006.01) | |
| *B01D 61/02* | (2006.01) | |
| *C12P 7/10* | (2006.01) | |

(52) U.S. Cl.
CPC ................ *D21B 1/02* (2013.01); *B01D 61/022* (2013.01); *C12P 7/10* (2013.01); *D21C 1/02* (2013.01); *D21C 1/04* (2013.01); *D21C 11/0042* (2013.01); *C12P 2201/00* (2013.01); *Y02E 50/16* (2013.01)

(58) Field of Classification Search
CPC ............... D21C 1/00; D21C 1/02; D21C 1/04
USPC ....................................................... 162/42, 43
See application file for complete search history.

(56) References Cited

U.S. PATENT DOCUMENTS

| | | | |
|---|---|---|---|
| 3,544,422 A * | 12/1970 | Zachariasen et al. | ........... 162/82 |
| 8,785,155 B2 * | 7/2014 | Retsina et al. | ................. 435/72 |
| 2009/0305374 A1 | 12/2009 | Retsina et al. | |

FOREIGN PATENT DOCUMENTS

| | | |
|---|---|---|
| WO | 03/040380 A2 | 5/2003 |
| WO | WO 2010046532 A1 * | 4/2010 |
| WO | WO 2013098789 A1 * | 7/2013 |

OTHER PUBLICATIONS

Wickramasinghe S R, et al., "Adsorptive membranes and resins for acetic acid removal from biomass hydrolysates", Desalination, Dec. 31, 2008, pp. 144-151, vol. 234, No. 1-3, Elsevier, Amsterdam, NL.
Han B, et al., "Adsorptive membranes vs. resins for acetic acid removal from biomass hydrolysates", Desalination, May 10, 2006, pp. 361-366, vol. 193, No. 1-3, Elsevier, Amsterdam, NL.
Han I S, et al., "Nanofiltration of model acetate solutions", Journal of Membrane Science, Nov. 15, 1995, pp. 107-113, vol. 107, No. 1, Elsevier, Amsterdam, NL.

* cited by examiner

*Primary Examiner* — Anthony Calandra
(74) *Attorney, Agent, or Firm* — Edwin A. Sisson, Attorney at Law, LLC; Jeffrey J. Banyas

(57) ABSTRACT

The process for treating a ligno-cellulosic biomass feed stream comprised of solids, C5's, C6's, lignin, and water comprises the steps of:
pretreating the ligno-cellulosic biomass feed stream by contacting the ligno-cellulosic biomass with water in the temperature range of 40 to 210° C. to create a pre-treated ligno-cellulosic biomass comprised of a pre-treatment ligno-cellulosic biomass liquid comprised of suspended solids, C5's, C6's, and acetic acid, wherein the ratio of the C6's to C5's is less than 0.8 to 1.0, and a pre-treated ligno-cellulosic biomass solids;

separating a portion of the pre-treatment ligno cellulosic biomass liquid from the pre-treated ligno-cellulosic biomass feed stream;

separating a portion of the suspended solids from the pre-treatment ligno-cellulosic biomass liquid using filters, centrifuge or combination thereof, to create a clarified liquid stream, and nano filtering a portion of the clarified liquid stream to create a nano-filtered permeate stream comprised of acetic acid and water and a nano-filtered retentate stream comprised of C5's, C6's, acetic acid and water, wherein the ratio of acetic acid to the total amount of C5's, C6's in the clarified liquid stream is greater than the ratio of the acetic acid to the total amount of C5's, C6's in the nano-filtered retentate.

3 Claims, 1 Drawing Sheet

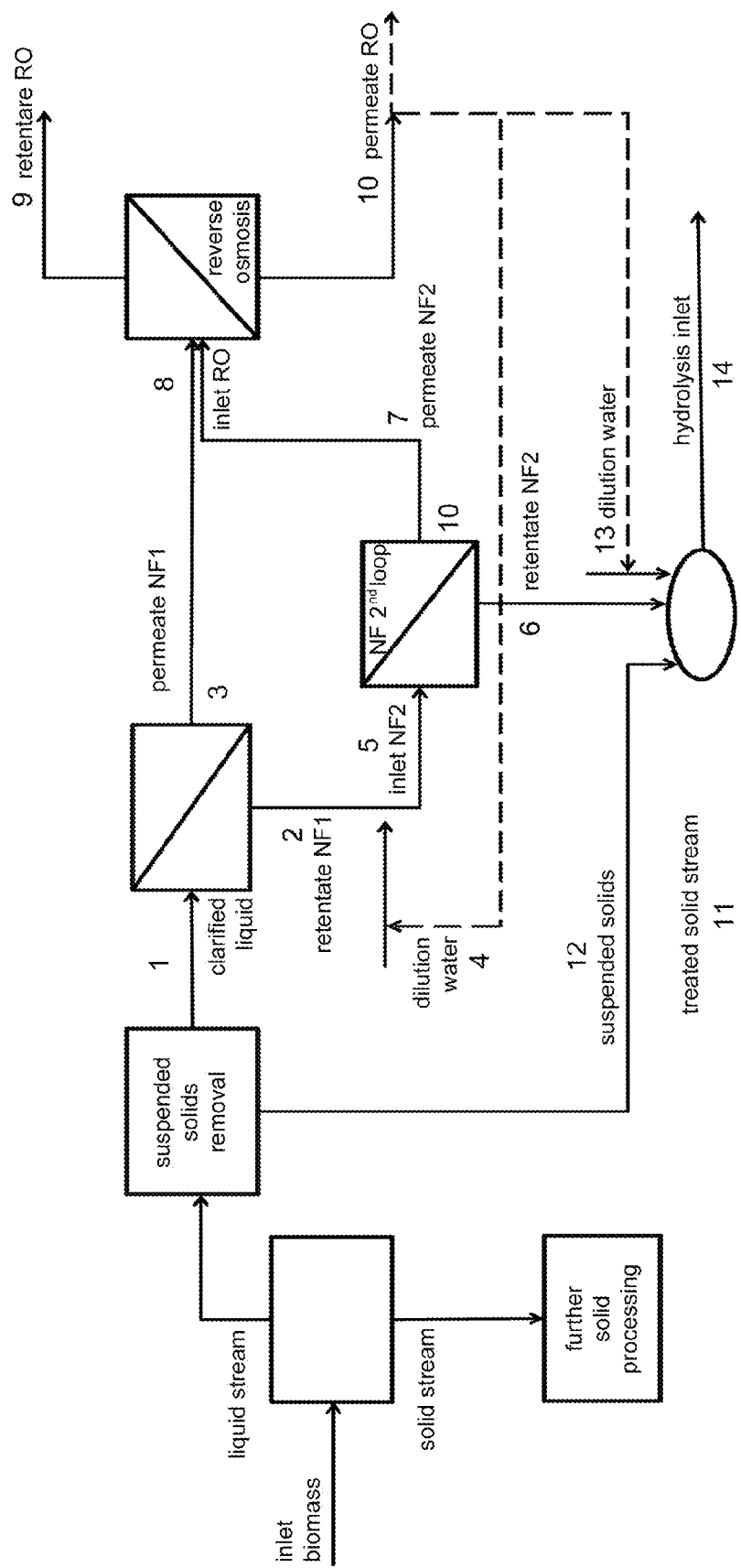

PROCESS FOR ACETIC ACID REMOVAL FROM PRETREATED BIOMASS

PRIORITY AND CROSS REFERENCES

This patent application claims the priority from PCT/IB2012/052490 filed on 17 May 2012 which claims priority from Italian Patent Application Number TO2011A000441 filed on 18 May 2011, the teachings of both of which are incorporated in their entirety.

BACKGROUND

It is known in the processing of ligno-cellulosic biomass to pretreat the biomass prior to hydrolysis or fermentation. This pre-treatment can be in the form of soaking the ligno-cellulosic biomass and separating the water soluble (C5) species in the liquid stream from the solids, and steam exploding the solid stream, or just steam exploding the ligno-cellulosic biomass stream.

Because the pre-treatments are aggressive, they create by-products such as acetic acid and furfural. A large amount of effort has been spent on trying to remove the acetic acid and/or furfural after pre-treatment as these chemicals inhibit and suppress further processing such as fermentation.

To date, no one has successfully managed to remove the acetic acid from a pre-treated stream of ligno-cellulosic biomass.

SUMMARY

This specification discloses a process for the removal of acetic acid from a pre-treated ligno-cellulosic biomass, which is a process for treating a ligno-cellulosic biomass feed stream comprised of solids, C5's, C6's, lignin, and water, comprising the steps of
  A) Pretreating the ligno-cellulosic biomass feed stream by contacting the ligno-cellulosic biomass with water in the temperature range of 40 to 210° C. to create a pre-treated ligno-cellulosic biomass comprised of a pre-treatment ligno-cellulosic biomass liquid comprised of suspended solids, C5's, C6's, and acetic acid, wherein the ratio of the C6's to C5's is less than 0.8 to 1.0, and a pre-treated ligno-cellulosic biomass solids,
  B) Separating at least a portion of the pre-treatment ligno cellulosic biomass liquid from the pre-treated ligno-cellulosic biomass feed stream,
  C) Separating at least a portion of the suspended solids from the pre-treatment ligno-cellulosic biomass liquid using filters, centrifuge or combination thereof, to create a clarified liquid stream,
  D) Nano filtering at least a portion of the clarified liquid stream to create a nano-filtered permeate stream comprised of acetic acid and water and a nano-filtered retentate stream comprised of C5's, C6's, acetic acid and water, wherein the ratio of acetic acid to the total amount of C5's, C6's in the clarified liquid stream is greater than the ratio of the acetic acid to the total amount of C5's, C6's in the nano-filtered retentate.

It is further disclosed that the nano-filtered permeate stream can be dewatered by reverse osmosis to create a reverse osmosis permeate comprised of water and reverse osmosis retentate comprised of water and acetic acid.

It is also further disclosed that the reverse osmosis permeate may be further used in a hydrolysis process or reused in the pre-treatment process and that the acetic acid of the reverse osmosis retenate is further used in a hydrolysis process.

It is also disclosed that the ligno-cellulosic biomass feedstream has not been steam exploded.

BRIEF DESCRIPTION OF THE FIGURES

FIG. 1 is a schematic representation of the embodied process.

DETAILED DESCRIPTION

This specification discloses a process to remove the acetic acid from a pre-treated ligno-cellulosic biomass stream.

The pretreated biomass usually comes from a lignocellulosic biomass or lignocellulosic compounds which has been pretreated by means of a process where the biomass, chosen as a preferred feedstock that is usually a plant biomass with cellulose, hemicelluloses and lignin, is soaked with water and maintained for a certain time at a certain temperature to obtain the pretreated biomass with a dry content and a water portion.

Because the feedstock may use naturally occurring ligno-cellulosic biomass, the stream will have relatively young carbon materials. The following, taken from ASTM D 6866-04 describes the contemporary carbon, which is that found in bio-based hydrocarbons, as opposed to hydrocarbons derived from oil wells, which was derived from biomass thousands of years ago. "[A] direct indication of the relative contribution of fossil carbon and living biospheric carbon can be as expressed as the fraction (or percentage) of contemporary carbon, symbol $f_C$. This is derived from $f_M$ through the use of the observed input function for atmospheric $^{14}C$ over recent decades, representing the combined effects of fossil dilution of the $^{14}C$ (minor) and nuclear testing enhancement (major). The relation between $f_C$ and $f_M$ is necessarily a function of time. By 1985, when the particulate sampling discussed in the cited reference [of ASTM D 6866-04, the teachings of which are incorporated by reference in their entirety] the $f_M$ ratio had decreased to ca. 1.2."

Fossil carbon is carbon that contains essentially no radiocarbon because its age is very much greater than the 5730 year half life of $^{14}C$. Modern carbon is explicitly 0.95 times the specific activity of SRM 4990b (the original oxalic acid radiocarbon standard), normalized to $\delta^{13}C=-19\%$. Functionally, the faction of modern carbon=(1/0.95) where the unit 1 is defined as the concentration of $^{14}C$ contemporaneous with 1950 [A.D.] wood (that is, pre-atmospheric nuclear testing) and 0.95 are used to correct for the post 1950 [A.D.] bomb $^{14}C$ injection into the atmosphere. As described in the analysis and interpretation section of the test method, a 100% $^{14}C$ indicates an entirely modern carbon source, such as the products derived from this process. Therefore, the percent $^{14}C$ of the product stream from the process will be at least 75%, with 85% more preferred, 95% even preferred and at least 99% even more preferred and at least 100% the most preferred. (The test method notes that the percent $^{14}C$ can be slightly greater than 100% for the reasons set forth in the method). These percentages can also be equated to the amount of contemporary carbon as well.

Therefore the amount of contemporary carbon relative to the total amount of carbon is preferred to be at least 75%, with 85% more preferred, 95% even more preferred and at least 99% even more preferred and at least 100% the most preferred. Correspondingly, each carbon containing compound in the reactor, which includes a plurality of carbon containing conversion products will have an amount of contemporary carbon relative to total amount of carbon is preferred to be at least 75%, with 85% more preferred, 95% even preferred and at least 99% even more preferred and at least 100% the most preferred.

In general, a natural or naturally occurring ligno-cellulosic biomass can be one feed stock for this process. Ligno-cellulosic materials can be described as follows:

Apart from starch, the three major constituents in plant biomass are cellulose, hemicellulose and lignin, which are commonly referred to by the generic term lignocellulose. Polysaccharide-containing biomasses as a generic term include both starch and ligno-cellulosic biomasses. Therefore, some types of feedstocks can be plant biomass, polysaccharide containing biomass, and ligno-cellulosic biomass.

Polysaccharide-containing biomasses according to the present invention include any material containing polymeric sugars e.g. in the form of starch as well as refined starch, cellulose and hemicellulose.

Relevant types of naturally occurring biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used to derive the composition is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indiangrass, bermuda grass and switch grass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis*; 3) Puelioideae a small lineage that includes the African genus *Puelia*; 4) Pooideae which includes wheat, barley, oats, brome-grass (*Bronnus*) and reed-grasses (*Calamagrostis*); 5) Bambusoideae which includes bamboo; 6) Ehrhartoideae, which includes rice, and wild rice; 7) Arundinoideae, which includes the giant reed and common reed; 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses; 11) Micrairoideae and 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Another naturally occurring ligno-cellulosic biomass feedstock may be woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium.

What is usually called "wood" is the secondary xylem of such plants.

The two main groups in which secondary xylem can be found are:
1) conifers (Coniferae): there are some six hundred species of conifers. All species have secondary xylem, which is relatively uniform in structure throughout this group. Many conifers become tall trees: the secondary xylem of such trees is marketed as softwood.
2) angiosperms (Angiospermae): there are some quarter of a million to four hundred thousand species of angiosperms. Within this group secondary xylem has not been found in the monocots (e.g. Poaceae). Many non-monocot angiosperms become trees, and the secondary xylem of these is marketed as hardwood.

The term softwood is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scale like leaves. They include conifer species e.g. pine, spruces, firs, and cedars. Wood hardness varies among the conifer species.

The term hardwood is used to describe wood from trees that belong to the angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore a preferred naturally occurring ligno-cellulosic biomass may be selected from the group consisting of the grasses and woods. Another preferred naturally occurring ligno-cellulosic biomass can be selected from the group consisting of the plants belonging to the conifers, angiosperms, Poaceae and families. Another preferred naturally occurring ligno-cellulosic biomass may be that biomass having at least 10% by weight of it dry matter as cellulose, or more preferably at least 5% by weight of its dry matter as cellulose.

The carbohydrate(s) comprising the invention is selected from the group of carbohydrates based upon the glucose, xylose, and mannose monomers and mixtures thereof.

The water of the feedstock is usually present in the form of water absorbed into the biomass itself and in the form of free water. The term biomass and water means the dry content of the biomass plus all the water which includes the water present prior to pre-treatment and the adsorbed water and the free water which have been added during the pretreatment process.

The pre-treated biomass can be characterized on the basis of its water, C5, C6, acetic acid, formic acid and furfural. The total C5's of the composition is the sum of arabinan and xylan in the composition which includes the monomers, dimers, oligomers and polymers of arabinose and xylose in the liquid and solid of the composition. The total C6's in the composition is the glucan content which includes the monomers, dimers, oligomers and polymers of glucose that may be present in the liquid and solids of the streams.

The pretreated biomass stream undergoes a separation step where the pretreated liquid biomass stream is separated in liquid form from the pretreated biomass using filter(s), centrifuge(s), press(es) or membrane or any other procedure able to separate a liquid stream from solids. The pre-treated liquid biomass stream should have a ratio by weight of total C6's to total C5's of less than 0.8 to 1.0, with less than 0.5 to 1.0 more preferred, less than 0.25 to 1 even more preferred, less than 0.1 to 1.0 even more preferred, and 0 to 1.0 being the most preferred. This is an example of a pretreated biomass liquid stream.

During the pretreatment step other organic compounds are usually formed or extracted from the biomass. These compounds usually derive from the cellulose or from the hemicellulose or from the lignin portions. In some cases, other organic compounds are present in the pretreated biomass stream due to organic compounds like starch or extractives in the inlet biomass feedstock to the pretreated process. These organic compounds, such as furfural, formic acid, and acetic acid, or at least a portion of them can be separated and collected in the pretreated biomass liquid stream.

The process described below has been able to remove one or more organic compounds of interest like the acetic acid from the pretreated liquid biomass stream.

One pre-treated stream of interest is the liquid stream obtained by water soaking the ligno-cellulosic biomass stream and removing the liquid. This stream will comprise water, some solids, acetic acid, and water soluble C5's as described above.

The pre-treated liquid ligno-cellulosic biomass stream comprising water, solids, acetic acid and C5's first undergoes a solids separation step. While any solid separation step is believed to work, it must be efficient enough to remove the solids that would otherwise destroy the membrane filtration process downstream. The preferred separation was done by centrifugation. After centrifugation, the liquid stream is nano-filtered. The centrifugation was done on an Alfa Laval Model LAB102B, with an operating velocity of 8800 rpm, having a volume of 0.1 liter and a maximum cake volume of 0.2 liter. The tests were operated between 50 and 100 liter/h with the best separation occurring in the range of 50-75 liter/h in which the suspended solids were reduced from 1.5% volume to 0% volume. Operating at higher than 75 liter/h left traces of suspended solids in the clarified liquid.

The nanofiltration step was conducted by passing the centrifuged stream over a membrane of polyamide type thin film composite on polyester having a MgSO4 rejection of 99%. This membrane is available from Alfa-Laval under the designation of NF99HF. The centrifuged stream should have a pH in the range of 2-10, and the nanofiltration conducted under a pressure in the range of about 1-55 bar and a temperature in the range of about 0-50° C. Two streams are created, a permeate stream and a retentate stream. In this specification, the permeate of the nano-filtration step is called the nano-filtered permeate stream and is comprised primarily of acetic acid and water. The material which does not pass through, or permeate, the membrane is called the retentate and is referred to as the nano-filtered retentate. Because the acetic acid and water pass through the membrane, the concentration of the acetic acid in the nano-filtered permeate stream is greater than the acetic concentration in the nano-filtered retentate stream.

The nano-filtered permeate stream comprised primarily of water and acetic acid was then subjected to reverse osmosis to separate substantially pure water from the permeate nano-filtered stream. The reverse osmosis occurs over a member thinfilm composite on polypropylene support paper having a NaCl rejection of greater than 96%. This type of membrane is available from Alfa-Laval under the designation of RO98pHt. The pH of the nano-filtered permeate stream during reverse osmosis is preferably in the range of 2-11, with the reverse osmosis preferably occurring under a pressure in the range of about 1-60 bar and a temperature preferably in the range of about 0-60° C.

The reverse osmosis permeate will be comprised almost entirely of water with the acetic acid concentration of the reverse osmosis retentate being greater than the acetic acid concentration of the reverse osmosis permeate.

The water of the reverse osmosis permeate can then be recycled back into the process, which for a second generation biomass facility is preferably the hydrolysis step.

FIG. 1 shows a typical unit operation process as described. The liquid stream feeds the process at 0.29 tonnes/h of acetic acid. After nano-filtration, the nano-filtered permeate has 0.2 ton per hour acetic acid, and after reverse osmosis, the reverse osmosis permeate has 0 tonnes of acetic per hour which is passed onto the viscosity reduction feeder. As the nano-filtered retentate will have some acetic acid (0.08 tonnes/hour), that is the only amount passed onto the hydrolysis/fermentation step. Thus, in this single step nano-filtration process, approximately 75% of the acetic acid was removed.

The nano-filtered retentate could be further filtered by either nano-filtration or reverse osmosis to further remove the remaining acetic acid.

While the above examples are exemplary of the invention, variants exist which are within the scope of inventor's invention as set forth in the claims.

EXPERIMENTAL

The following experiment evidences the different aspects of the disclosed invention.

FIG. 1 reports a diagram showing the experimental procedure and the flows obtained in the experiment.

Raw material (wheat straw) was introduced in a continuous reactor and subjected to soaking treatment at a temperature of 155° C. for 65 minutes. The soaked mixture was separated by means of a press in a liquid stream and a soaked stream containing the soaked solid raw material. The fraction containing the solid soaked raw material was subjected to steam explosion at a temperature of 190° C. for a time of 4 minutes to produce a steam exploded stream.

The liquid from the soaking comprised of suspended and unsuspended solids was subjected to a solid separation step to remove solids, by means of centrifugation and micro-filtration (bag filter with filter size of 1 micron). Centrifugation was performed by means of a Alfa Laval CLARA 80 centrifuge at 8000 rpm. A clarified liquid was separated from suspended solids.

The clarified liquid was then subjected to a first nano-filtration step by means of a Alfa Laval 3.8" equipment (membrane code NF3838/48), according to the following procedure.

Permeate flow stability was checked by means of flushing with de-mineralized water, at the temperature of 50° C. and 10 bar. The flow rate of the permeate was measured. An amount of 1800 liter of clarified liquid were inserted in the feed tank. Before filtration, the system was flushed for 5 minutes, without pressure, in order to remove the water. The system was set at the operating conditions (pressure: 20 bar, temperature: 45° C.). The retentate stream was recycled to the feed tank and the permeate stream was dumped. The test was run until the volume of liquid in the feed tank was reduced up to 50% of the initial soaked liquid volume, corresponding to 900 liters of permeate and 900 liters of retentate. The previous procedure produced a first nano-filtered retentate NF1-R and a first nano-filtered permeated NF1-P.

The first retentate liquid NF1-R was diluted by adding a volume of water corresponding to 50% of volume of NF1-R. The diluted NF1-R, indicated as inlet NF2, was subjected to a second first nano-filtration step, according to the same procedure used in the first nano-filtration step. In this case, an amount of 1350 liter of inlet NF2 was inserted in the feed tank and the test was run until the volume of liquid in the feed tank was reduced up to 40.0% of the initial soaked liquid volume, corresponding to 540 liters of permeate and 810 liters of retentate.

The second nano-filtration produced a second nano-filtered retentate NF2-R and a second nano-filtered permeated NF2-P.

Nano-filtered permeates NF1-P and NF2-P were mixed to form inlet RO liquid, which was subjected to reverse osmosis by means of a Alfa Laval 2.5" equipment (membrane code RO98pHt), according to the following procedure.

Permeate flow stability was checked by means of flushing with de-mineralized water, at room temperature (25° C.) and 10 bar. The flow rate of the permeate was measured. An amount of 192 liter of inlet RO liquid was inserted in the feed tank. Liquid pH was adjusted to 6 with a KOH diluted solution. Before filtration, the system was flushed for 5 minutes, without pressure, in order to remove the water. The system was set at the operating conditions (pressure: 30 bar, temperature: 50° C.). The retentate stream was recycled to the feed tank and the permeate stream was dumped. The test was run until the volume of liquid in the feed tank was reduced up to 33.3% of the initial pre-nano-filtrated liquid volume, corresponding to 128 liters of permeate and 64 liters of retentate.

The reverse osmosis produced a retentate RO and a permeate RO.

Suspended solids, steam exploded stream, permeate RO and retentate NF2-R were mixed to form the hydrolysis inlet.

Table 1 presents the concentrations of sugars and acetic acid in the flows marked 1 to 14 in FIG. 1. Sugars are monomeric and oligomeric sugars which were solubilized.

According to the disclosed invention, the acetic acid to sugar ratio in NF-2R is lower than the ratio in clarified liquid.

The table presents also the flows relative to a continuous process, extrapolated from the experimental data, for a clarified liquid flow of 50 t/h.

TABLE 1

| # | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| stream | clarified liquid | retentate NF1-R | permeate NF1-P | dilution water | inlet NF2 | retentate NF2-R | permeate NF2-P | inlet RO | retentate RO | permeate RO | steam exploded stream | suspended solids | dilution water | hydrolysis inlet |
| total mass flow (t/h) | 50.0 | 24.9 | 25.0 | 12.5 | 37.4 | 8.9 | 22.4 | 47.4 | 10.5 | 31.6 | 23.3 | 1.2 | 13.7 | 47.0 |
| liquid mass flow (t/h) | 50.0 | 24.9 | 25.0 | 12.5 | 37.4 | 8.9 | 22.4 | 47.4 | 10.5 | 31.6 | 14.0 | 1.0 | 13.7 | 37.6 |
| sugars flow (t/h) | 1.28 | 1.21 | 0.00 | | 1.21 | 1.15 | 0.00 | 0.00 | 0.00 | 0.00 | 0.07 | 0.03 | | 1.2 |
| acetic acid flow (t/h) | 0.13 | 0.07 | 0.06 | | 0.07 | 0.03 | 0.04 | 0.09 | 0.09 | 0.00 | 0.00 | 0.00 | | 0.0 |
| sugars concentration (g\l) | 25.5 | 48.6 | 0.0 | | 32.4 | 129.1 | 0.0 | 0.0 | 0.0 | 0.0 | 5.0 | 25.5 | | 26.5 |
| acetic acid concentration (g\l) | 2.5 | 2.8 | 2.3 | | 1.8 | 3.5 | 1.7 | 2.0 | 8.9 | 0.0 | 0.2 | 2.5 | | 0.8 |
| acetic acid/ sugars ratio | 0.10 | 0.06 | | | 0.06 | 0.03 | | | | | | | | 0.03 |

We claim:

1. A process for treating a ligno-cellulosic biomass feed stream comprised of solids, C5's, C6's, lignin, and water, wherein said process comprises the steps of:
   A) Pretreating the ligno-cellulosic biomass feed stream by contacting the ligno-cellulosic biomass with water in the temperature range of 40 to 210° C. to create a pre-treated ligno-cellulosic biomass comprised of a pre-treatment ligno-cellulosic biomass liquid comprised of suspended solids, C5's, C6's, and acetic acid, wherein the weight ratio of the C6's to C5's is in the range of between 0.1 to 1.0 and 0.8 to 1.0, and a pre-treated ligno-cellulosic biomass solids,
   B) Separating at least a portion of the pre-treatment ligno-cellulosic biomass liquid from the pre-treated ligno-cellulosic biomass feed stream,
   C) Separating at least a portion of the suspended solids from the pre-treatment ligno-cellulosic biomass liquid using filters, centrifuge or combination thereof, to create a clarified liquid stream,
   D) A first Nano filtering of at least a portion of the clarified liquid stream to create a first nano-filtered permeate stream comprised of acetic acid and water and a first nano-filtered retentate stream comprised of C5's, C6's, acetic acid and water, wherein the weight ratio of acetic acid to the total amount of C5's, C6's in the clarified liquid stream is greater than the ratio of the acetic acid to the total amount of C5's, C6's in the first nano-filtered retentate,
   E) A second Nano filtering of at least a portion of the first nano-filtered retentate to create a second nano-filtered permeate stream comprised of acetic acid and water and a second nano-filtered retentate stream comprised of C5's, C6's, acetic acid and water,
   F) Dewatering the first nano-filtered permeate stream and the second nano-filtered permeate stream by reverse osmosis to create a reverse osmosis permeate comprised of water and a reverse osmosis retentate comprised of water and acetic acid,
   G) Using at least a portion of the water from the reverse osmosis permeate as dilution water for the second nano-filtering.

2. The process according to claim 1, wherein the acetic acid of the reverse osmosis retentate is further used in a hydrolysis process.

3. The process according to claim 1, wherein the ligno-cellulosic biomass feedstream has not been steam exploded.

* * * * *